(12) United States Patent
Perrine

(10) Patent No.: US 9,095,565 B2
(45) Date of Patent: Aug. 4, 2015

(54) METHODS FOR TREATING BLOOD DISORDERS

(71) Applicant: Phoenicia Biosciences, Inc., Weston, MA (US)

(72) Inventor: Susan P. Perrine, Weston, MA (US)

(73) Assignee: Phoenicia Biosciences, Inc., Weston, MA (US)

( * ) Notice: Subject to any disclaimer, the term of this patent is extended or adjusted under 35 U.S.C. 154(b) by 0 days.

(21) Appl. No.: 14/310,955

(22) Filed: Jun. 20, 2014

(65) Prior Publication Data
US 2014/0301975 A1 Oct. 9, 2014

Related U.S. Application Data

(63) Continuation-in-part of application No. 12/212,000, filed on Sep. 17, 2008, now Pat. No. 8,759,378, which is a continuation of application No. 11/746,543, filed on May 9, 2007, now abandoned.

(60) Provisional application No. 60/799,054, filed on May 9, 2006.

(51) Int. Cl.
| | | |
|---|---|---|
| *A61K 31/37* | (2006.01) | |
| *A61K 31/433* | (2006.01) | |
| *C07D 285/125* | (2006.01) | |
| *C07D 311/12* | (2006.01) | |

(52) U.S. Cl.
CPC ............... *A61K 31/37* (2013.01); *A61K 31/433* (2013.01); *C07D 285/125* (2013.01); *C07D 311/12* (2013.01)

(58) Field of Classification Search
None
See application file for complete search history.

(56) References Cited

U.S. PATENT DOCUMENTS 4,021,559 A  *  5/1977  Giudicelli et al. ............ 514/283

FOREIGN PATENT DOCUMENTS

| DE | 959402 | * | 3/1957 | |
| WO | WO 95/24189 | * | 9/1995 | ........... A61K 31/265 |

* cited by examiner

*Primary Examiner* — Bethany Barham
*Assistant Examiner* — Barbara Frazier
(74) *Attorney, Agent, or Firm* — Remenick PLLC

(57) ABSTRACT

Methods of treating blood disorders are described.

25 Claims, No Drawings

METHODS FOR TREATING BLOOD DISORDERS

CROSS-REFERENCE TO RELATED APPLICATION

This application is a continuation-in-part of U.S. application Ser. No. 12/212,000 filed Sep. 17, 2008, which is a continuation of U.S. patent application Ser. No. 11/746,543, filed May 9, 2007, entitled "Methods for Treating Blood Disorders," which claims the benefit under 35 U.S.C. §119(e) of U.S. Provisional Patent Application No. 60/799,054 filed May 9, 2006, which are each incorporated herein by reference in their entirety.

BACKGROUND

1. Field of the Invention

The present invention relates to methods and compounds for the treatment of blood disorders.

2. Description of the Related Art

The major function of red blood cells is to transport oxygen to tissues of the body, while minor functions include the transportation of nutrients and cytokines and the absorption of cellular metabolites. Anemia, defined as a loss of red blood cells or red blood cell capacity resulting in the reduction in the ability of the blood to transport oxygen, may be chronic or acute. Chronic anemia may be caused by extrinsic red blood cell abnormalities, intrinsic abnormalities or impaired production of red blood cells. Extrinsic or extra-corpuscular abnormalities include antibody-mediated disorders such as transfusion reactions and erythroblastosis, mechanical trauma to red cells such as micro-angiopathic hemolytic anemias, thrombotic thrombocytopenic purpura and disseminated intravascular coagulation. In addition, infections by parasites such as Plasmodium, chemical injuries from, for example, lead poisoning, and sequestration in the mononuclear system such as by hyperspienism can result in red blood cell disorders and deficiencies.

Impaired red blood cell production can occur by disturbing the proliferation and differentiation of the stem cells or committed cells. Some of the more common diseases of red cell production include aplastic anemia, sickle cell anemia, β-thalassemia, hypoplastic anemia, pure red cell aplasia and anemia associated with renal failure or endocrine disorders. Disturbances of the proliferation and differentiation of erythroblasts include defects in DNA synthesis such as impaired utilization of vitamin $B_{12}$ or folic acid and the megaloblastic anemias, defects in heme or globin synthesis, and anemias of unknown origins such as sideroblastic anemia, anemia associated with chronic infections such as malaria, trypanosomiasis, HIV, hepatitis virus or other viruses, and myelophthisic anemias caused by marrow deficiencies.

Symptoms of anemia include feelings of weakness or fatigue, pallor, shortness of breath, an increase in cardiac output, which may lead to palpitations and sweatiness. In severe cases, anemia can lead to death by heart failure. Current treatments for anemia depend on the type of anemia the patient suffers from. Monitoring of the diet to increase iron intake may be prescribed, as well as iron supplementation. In some cases, medication or blood transfusions may be necessary.

Sickle cell disease and β-thalassemia are two of the most common genetic disorders in the word. These disorders are caused by molecular mutations affecting the β-globin genes for adult hemoglobin A (α2β2), and it has been established that these disorders can be ameliorated by reactivating production of fetal hemoglobin (HbF, α2γ2) in the patients' blood. Even small increments in fetal hemoglobin decreases morbidity and mortality in sickle cell disease, while higher levels are necessary to completely ameliorate the symptoms. In β-thalassemia, increases in fetal globin synthesis, which reduces the excess unbalanced α-globin chains by 10%, is often enough to decrease the anemia to a level which does not require regular blood transfusions.

Short chain fatty acids and derivatives of 2-9 carbons induce expression of γ-globin in cultured erythroid cells, animal models and reporter gene assays, which test activity in activating the γ-globin gene promoter. Several short chain fatty acids induce the γ-globin promoter and have biologic and clinical activity. Pharmacological re-introduction of HbF has been achieved in patients with a prototype short-chain fatty acid, arginine butyrate, resulting in sufficient levels of HbF to ameliorate anemia and reduce clinical complications. Patients treated in a Phase II trial with pulsed butyrate have experienced both biochemical and clinical improvement in their diseases, with excellent safety profiles. However, the prototype short chain fatty acids have limitations as therapeutics. Arginine butyrate and phenylbutyrate require 100 μM levels in vitro and are rapidly metabolized in vivo, necessitating large quantities (20 g for sodium phenyl butyrate), an intravenous infusion for arginine butyrate and careful adjustment of dosing to prevent secondary suppression of erythopoiesis.

While advances have been made in this field, there remains a need for new and/or improved methods for treating and preventing blood disorders generally as well as for compounds and pharmaceutical compositions for the same.

BRIEF SUMMARY

The present invention pertains, at least in part, to methods for treating or preventing a blood disorder in a subject by administering to the subject an effective amount of a compound of formula I:

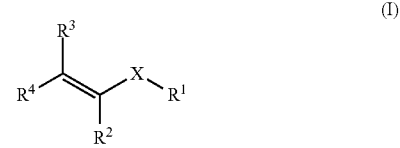

(I)

wherein $R^1$ is hydroxy or alkoxy;

X is C(O), C(S), SO, $SO_2$ or $PO_2$;

$R^2$ and $R^3$ are each independently hydrogen, alkyl, halogen, hydroxyl, thiol, alkenyl, alkynyl, aryl, acyl, alkoxy, amino, alkylamino or heterocyclic;

$R^4$ is alkyl, cycloalkyl, alkenyl, alkynyl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, heteroaryl, halogen or

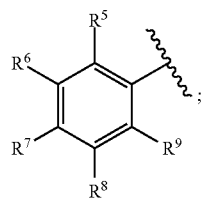

$R^5$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to $R^6$ to form a ring;

$R^6$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to $R^5$ or $R^7$ to form a ring;

$R^7$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to $R^6$ or $R^8$ to form a ring;

$R^8$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to $R^7$ or $R^9$ to form a ring;

$R^9$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to $R^8$ to form a ring;

and racemates, isolated enantiomers or diastereomers, and pharmaceutically acceptable salts thereof;

provided that when $R^4$ is

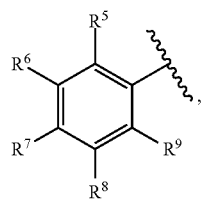

$R^5$, $R^6$, $R^7$, $R^8$, and $R^9$ are each not hydrogen; and when $R^6$, $R^7$, $R^8$, and $R^9$ are each hydrogen, $R^5$ is not methoxy; and when $R^5$, $R^7$, $R^8$, $R^9$ are hydrogen, $R^6$ is not methoxy; and when $R^5$, $R^8$ and $R^9$ are hydrogen, $R^6$ and $R^7$ are not methoxy.

In another embodiment, the present invention pertains, at least in part, to methods for treating or preventing a blood disorder in a subject by administering to the subject an effective amount of a compound of formula II:

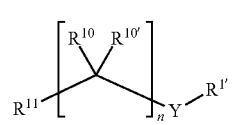

Wherein
$R^{1'}$ is hydroxy or alkoxy;
Y is C(O);
n is 0 or an integer from 1 to 5;
$R^{10}$ and $R^{10'}$ are each independently hydrogen, alkyl, halogen, hydroxyl, thiol, alkenyl, alkynyl, aryl, acyl, alkoxy, amino, alkylamino, heterocyclic or optionally joined to form a ring;

$R^{11}$ is $CR^{11'}R^{11''}R^{11'''}$, alkenyl, cycloalkyl, alkynyl, arylalkyl, amido, alkylamino, amino, arylamino, carbonylalkyl, alkylcarbonyl, arylcarbonyl, alkylaminocarbonyl, alkoxycarbonyl, alkylcarbonyloxy, alkyloxycarbonyloxy, arylcarbonyloxy, thiol, alkylthio, arylthio, alkenyl, heterocyclic, heteroaryl, hydroxy, halogen or

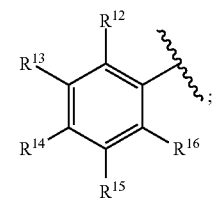

$R^{11'}$ and $R^{11''}$ are each independently hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxyl, halogen, or $R^{11'}$ and $R^{11''}$ are optionally joined to form a ring;

$R^{11'''}$ is alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy or halogen;

$R^{12}$ is hydrogen, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic or optionally linked to $R^{13}$ to form a ring;

$R^{13}$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy or optionally linked to $R^{12}$ or $R^{14}$ to form a ring;

$R^{14}$ is hydrogen, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, halogen or optionally linked to $R^{13}$ or $R^{15}$ to form a ring;

$R^{15}$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, halogen or optionally linked to $R^{14}$ or $R^{16}$ to form a ring;

$R^{16}$ is hydrogen, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, halogen or optionally linked to $R^{15}$ to form a ring;

and racemates, isolated enantiomers or diastereomers, and pharmaceutically acceptable salts thereof;

provided that when $R^{11}$ is

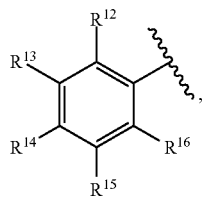

$R^{12}$, $R^{13}$, $R^{14}$, $R^{15}$, and $R^{16}$ are each not hydrogen; and provided when n is 2, $R^{11}$ is

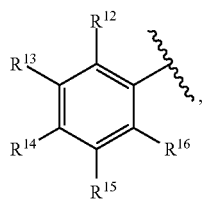

and $R^{10}$, $R^{10'}$, $R^{12}$, $R^{15}$, and $R^{16}$ are hydrogen, then $R^{14}$ and $R^{15}$ are not methoxy; and provided when n is 1, $R^{11}$ is

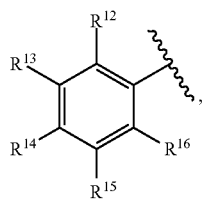

and $R^{10}$, $R^{10'}$, $R^{13}$, $R^{14}$, and $R^{16}$ are hydrogen, then $R^{12}$ and $R^{15}$ are not methoxy.

In yet another embodiment, the present invention pertains, at least in part, to methods for treating or preventing a blood disorder in a subject by administering to the subject an effective amount of a compound of formula III:

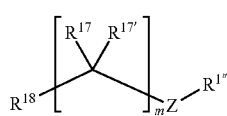

Wherein
$R^{1''}$ is hydroxy or alkoxy;
Z is C(S), SO, $SO_2$ or $PO_2$;
m is 0 or an integer from 1-5;

$R^{17}$ and $R^{17'}$ are each independently hydrogen, alkyl, halogen, hydroxyl, thiol, alkenyl, alkynyl, aryl, acyl, alkoxy, amino, alkylamino or heterocyclic;

$R^{18}$ is hydrogen, alkyl, cycloalkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, heteroaryl, hydroxyl or halogen;

and racemates, isolated enantiomers or diastereomers, and pharmaceutically acceptable salts thereof.

In another embodiment, the present invention pertains, at least in part, to methods for treating or preventing a blood disorder in a subject by administering to the subject an effective amount of a compound of formula:

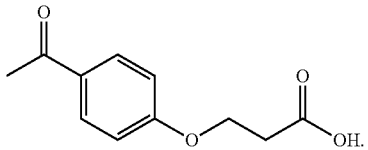

In one embodiment, the present invention pertains, at least in part, to pharmaceutical compositions of an effective amount of a compound of formula I, formula II, formula III, or

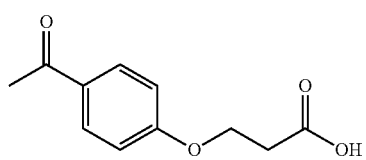

and a pharmaceutically acceptable carrier.

In another embodiment, the present invention pertains, at least in part, to compounds of formula I, formula II, and formula (III) and racemates, isolated enantiomers or diastereomers, and pharmaceutically acceptable salts thereof.

DETAILED DESCRIPTION

In one embodiment, the present invention pertains, at least in part, to methods
for treating or preventing a blood disorder in a subject by administering to the subject an effective amount of a compound of formula I:

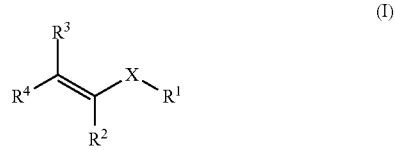

wherein
$R^1$ is hydroxy or alkoxy;
X is C(O), C(S), SO, $SO_2$ or $PO_2$;
$R^2$ and $R^3$ are each independently hydrogen, alkyl, halogen, hydroxyl, thiol, alkenyl, alkynyl, aryl, acyl, alkoxy, amino, alkylamino or heterocyclic;
$R^4$ is alkyl, cycloalkyl, alkenyl, alkynyl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, heteroaryl, halogen or

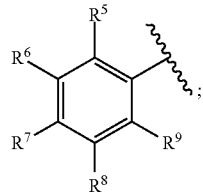

R⁵ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to R⁶ to form a ring;

R⁶ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to R⁵ or R⁷ to form a ring;

R⁷ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to R⁶ or R⁸ to form a ring;

R⁸ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to R⁷ or R⁹ to form a ring;

R⁹ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to R⁹ to form a ring;

and racemates, isolated enantiomers or diastereomers, and pharmaceutically acceptable salts thereof;

provided that when R⁴ is

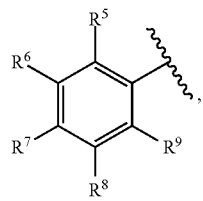

R⁵, R⁶, R⁷, R⁸, and R⁹ are each not hydrogen; and when R⁶, R⁷, R⁸, and R⁹ are each hydrogen, R⁵ is not methoxy; and when R⁵, R⁷, R⁸, R⁹ are hydrogen, R⁶ is not methoxy; and when R⁵, R⁸ and R⁹ are hydrogen, R⁶ and R⁷ are not methoxy.

In one embodiment, R¹ is hydroxy, X is C(O) and R⁴ is

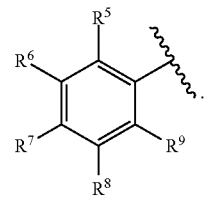

In one embodiment, R², R³, R⁵, R⁶, R⁸ and R⁹ are each hydrogen and R⁷ is alkoxy (e.g., methoxy).

In another embodiment, R², R³, R⁵, R⁷ and R⁸ are each hydrogen, and R⁶ and R⁹ are each alkyl (e.g., methyl).

In yet another embodiment, R², R³, R⁵, R⁸ are R⁹ are each hydrogen and R⁶ and R⁷ are each hydroxyl.

In a further embodiment, R², R³, R⁵, R⁸ are R⁹ are each hydrogen and R⁶ and R⁷ are linked by —O—CH₂—O— to form a ring.

In yet another embodiment, R², R³, R⁵, R⁶ and R⁹ are each hydrogen, R⁷ is alkoxy (e.g., methoxy) and R⁸ is hydroxyl.

In another embodiment, R¹ is hydroxy, X is C(O) and R⁴ is heteroaryl, such quinoline or substituted or unsubstituted thiophene (e.g., chlorothiophene).

In one embodiment, the present invention pertains, at least in part, to methods for treating or preventing a blood disorder in a subject by administering to the subject an effective amount of a compound of formula I, wherein the compound of formula I is:

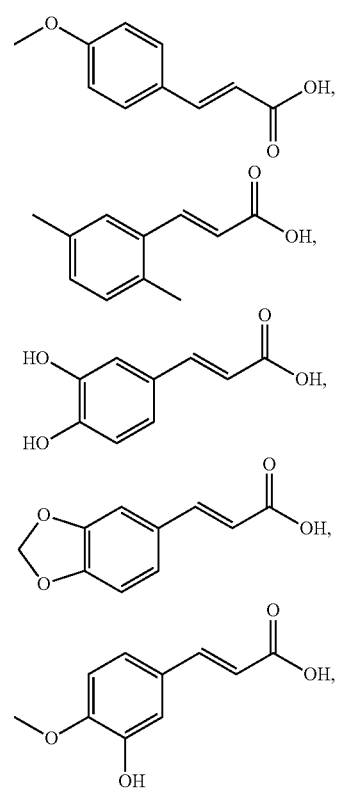

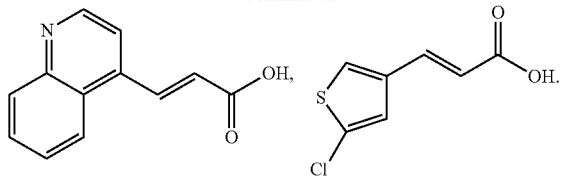

In another embodiment, the present invention pertains, at least in part, to methods for treating or preventing a blood disorder in a subject by administering to the subject an effective amount of a compound of formula II:

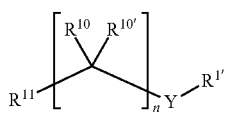

(II)

wherein
$R^{1'}$ is hydroxy or alkoxy;
Y is C(O);
n is 0 or an integer from 1 to 5;
$R^{10}$ and $R^{10'}$ are each independently hydrogen, alkyl, halogen, hydroxyl, thiol, alkenyl, alkynyl, aryl, acyl, alkoxy, amino, alkylamino, heterocyclic or optionally joined to form a ring;
$R^{11}$ is $CR^{11'}R^{11''}R^{11'''}$, alkenyl, cycloalkyl, alkynyl, arylalkyl, amido, alkylamino, amino, arylamino, carbonylalkyl, alkylcarbonyl, arylcarbonyl, alkylaminocarbonyl, alkoxycarbonyl, alkylcarbonyloxy, alkyloxycarbonyloxy, arylcarbonyloxy, thiol, alkylthio, arylthio, alkenyl, heterocyclic, heteroaryl, hydroxy, halogen or

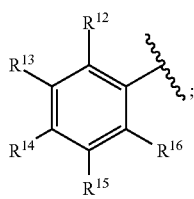

$R^{11'}$ and $R^{11'''}$ are each independently hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxyl, halogen or $R^{11'}$ and $R^{11'''}$ are optionally joined to form a ring;
$R^{11''}$ is alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy or halogen;
$R^{12}$ is hydrogen, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic or optionally linked to $R^{13}$ to form a ring;
$R^{13}$ is hydrogen, alkyl, alkenyl, alkynyl, aryl, arylalkyl, amido, alkylamino, amino, arylamino, alkylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy or optionally linked to $R^{12}$ or $R^{14}$ to form a ring;
$R^{14}$ is hydrogen, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, halogen or optionally linked to $R^{13}$ or $R^{15}$ to form a ring;
$R^{15}$ is hydrogen, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, halogen or optionally linked to $R^{14}$ or $R^{16}$ to form a ring;
$R^{16}$ is hydrogen, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, halogen or optionally linked to $R^{15}$ to form a ring;
and racemates, isolated enantiomers or diastereomers, and pharmaceutically acceptable salts thereof;
provided that when $R^{11}$ is

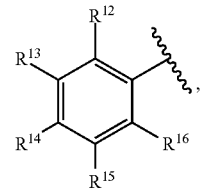

$R^{12}$, $R^{13}$, $R^{14}$, $R^{15}$, and $R^{16}$ are each not hydrogen; and provided when n is 2, $R^{11}$ is

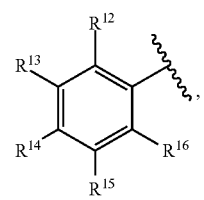

and $R^{10}$, $R^{10'}$, $R^{12}$, $R^{15}$, and $R^{16}$ are hydrogen, then $R^{14}$ and $R^{15}$ are not methoxy; and provided when n is 1, $R^{11}$ is

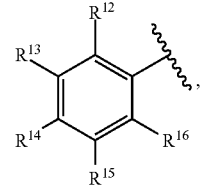

and $R^{10}$, $R^{10'}$, $R^{13}$, $R^{14}$, and $R^{16}$ are hydrogen, then $R^{12}$ and $R^{15}$ are not methoxy.
In one embodiment, $R^{1'}$ is hydroxyl, n is 5, $R^{10}$ and $R^{10'}$ are hydrogen and $R^{11}$ is alkylcarbonyl.
In another embodiment, $R^{1'}$ is hydroxyl, n is 2, $R^{10}$ and $R^{10'}$ are each hydrogen and $R^{11}$ is $CR^{11'}R^{11''}R^{11'''}$.

In a further embodiment, $R^{11'}$ and $R^{11'''}$ are joined by —$(CH_2)_5$— to form a cyclohexyl ring and $R^{11''''}$ is a substituted or unsubstituted heterocycle (e.g., chlorothiophene).

In one embodiment, $R^{1'}$ is hydroxyl, n is 0 and $R^{11}$ is

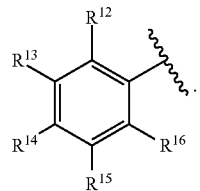

In one embodiment, $R^{13}$, $R^{14}$, $R^{15}$, and $R^{16}$ are hydrogen and $R^{12}$ is arylthioalkyl or alkoxy substituted aryloxy.

In another embodiment, $R^{12}$, $R^{14}$, $R^{15}$ and $R^{16}$ are hydrogen and $R^{13}$ is a substituted or unsubstituted heterocycle, such as, for example, chromen-2-one, nitro-substituted pyrazole, or chloro-substituted pyrazole.

In yet another embodiment, $R^{12}$, $R^{13}$, $R^{15}$ and $R^{16}$ are hydrogen and $R^{13}$ is alkoxy (e.g., ethoxy).

In a further embodiment, $R^{12}$, $R^{15}$ and $R^{16}$ are hydrogen, and $R^{13}$ and $R^{14}$ are linked by —N(H)C(O)$CH_2$S— to form a ring.

In yet another embodiment, $R^{14}$, $R^{15}$ and $R^{16}$ are each hydrogen, and $R^{12}$ and $R^{13}$ are linked by —CH=C($CH_3$)O— to form a ring.

In one embodiment, $R^{1'}$ is hydroxyl, n is 0 and $R^{11}$ is a substituted or unsubstituted heterocycle (e.g., substituted aryl-substituted furan) or a substituted or unsubstituted cycloalkyl (e.g., tetrahydrobenzothiadiazole or dihydrobenzothiophenone).

In one embodiment, $R^{1'}$ is hydroxyl, n is 1, $R^{10}$ and $R^{10'}$ are hydrogen and $R^{11}$ is a substituted or unsubstituted cycloalkyl (e.g., dimethylcyclobutane carboxylic acid).

In another embodiment, $R^{1'}$ is hydroxyl, n is 1, $R^{10}$ and $R^{10'}$ are hydrogen and $R^{11}$ is

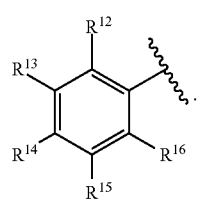

In one embodiment, $R^{12}$, $R^{13}$ and $R^{16}$ are hydrogen, and $R^{14}$ and $R^{15}$ are linked by —O—$CH_2$—O— to form a ring.

In another embodiment, $R^{1'}$ is hydroxyl, n is 1, $R^{10}$ and $R^{10'}$ are hydrogen and $R^{11}$ is a substituted or unsubstituted heterocycle, such as, for example substituted thiazolidinedione, substituted pyridinone or substituted pyrazole.

In yet another embodiment, $R^{1'}$ is hydroxyl, n is 1, $R^{10}$ and $R^{10'}$ are hydrogen and $R^{11}$ is a unsubstituted or substituted arylamino (e.g., trifluorothio-substituted arylamino).

In a further embodiment, $R^{1'}$ is hydroxyl, n is 1, $R^{10}$ and $R^{10'}$ are hydrogen and $R^{11}$ is unsubstituted or substituted arylthio (e.g., methoxyphenylthio) or unsubstituted or substituted heterocyclic thio, such as, for example, substituted triazolethio, substituted thiadiazolethio or substituted thiophenethio.

In another embodiment, $R^{1'}$ is hydroxyl, n is 1, $R^{10}$ and $R^{10'}$ are hydrogen and $R^{11}$ is $R^{11}$ is $CR^{11'}R^{11''}R^{11'''}$ and $R^{11'}$ is hydrogen, $R^{11'''}$ is amino and $R^{11''''}$ is alkoxy-substituted aryl.

In one embodiment, $R^{1'}$ is hydroxyl, n is 1, $R^{10}$ is hydrogen and $R^{10'}$ is alkyl. In one embodiment, $R^{10'}$ is isopropyl and $R^{11}$ is substituted or unsubstituted arylthio, such as, for example, alkoxy-substituted phenylthio or alkoxy-substituted pyrimadinylthio.

In another embodiment, $R^{10'}$ is ethyl and $R^{11}$ is heteroarylamino (e.g., quinazolinylamino).

In yet another embodiment, $R^{1'}$ is hydroxyl, n is 1, $R^{10}$ and $R^{10'}$ are linked by —$(CH_2)_5$— to form a cyclohexyl ring and $R^{11}$ is heterocyclic substituted carbonylalkyl.

In one embodiment, the compounds of formula (II) do not include compounds wherein $R^1$ is hydroxy, $R^{10}$ is alkyl, e.g., ethyl, $R^{10'}$ is hydrogen, n is 1, and $R^{11}$ is arylamino, e.g., quinazolin-4-ylamino.

In one embodiment, the compounds of formula (II) do not include compounds wherein $R^1$ is hydroxy, $R^{10}$ is hydrogen, $R^{10'}$ is alkyl, e.g., ethyl, n is 1, and $R^{11}$ is arylamino, e.g., quinazolin-4-ylamino.

In another embodiment, the compounds of formula (II) do not include compounds wherein $R^1$ is hydroxy, $R^{10}$ and $R^{10'}$ are each hydrogen, n is 1, and $R^{11}$ is aryl amino (e.g., trifluorothio-substituted arylamino).

In another embodiment, the compounds of formula (II) do not include 2-(quinazolin-4-ylamino)butyric acid or [4-[(trifluoromethyl)sulfanyl]-anilino]-acetic acid.

In one embodiment, the present invention pertains, at least in part, to methods for treating or preventing a blood disorder in a subject by administering to the subject an effective amount of a compound of formula II, wherein the compound of formula II is:

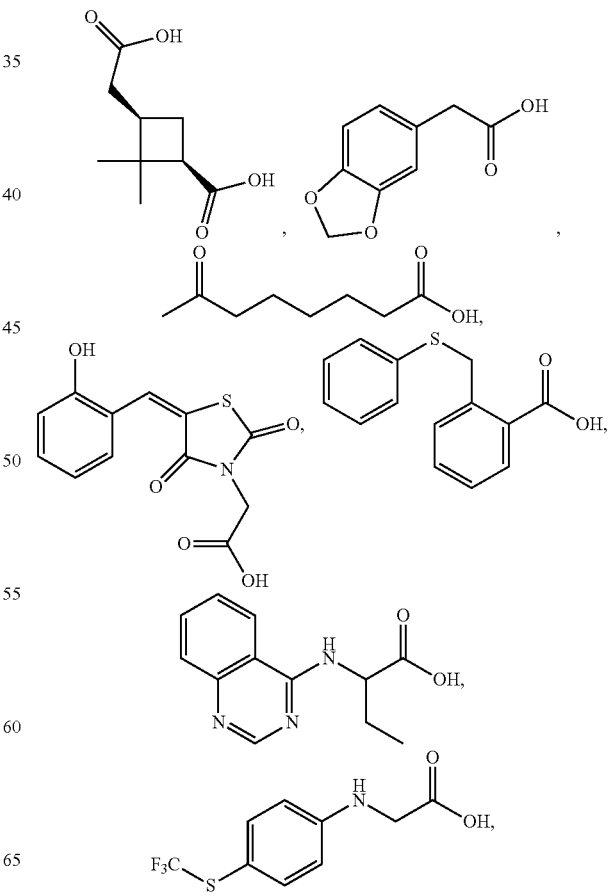

-continued
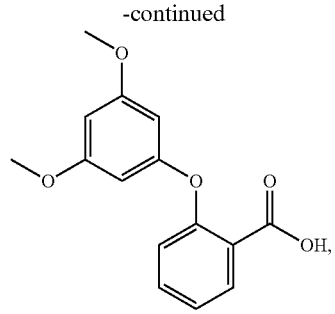
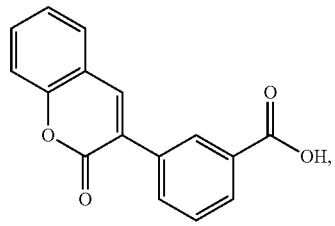
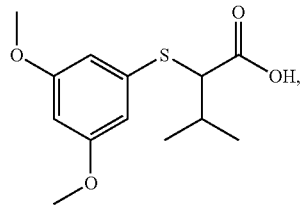
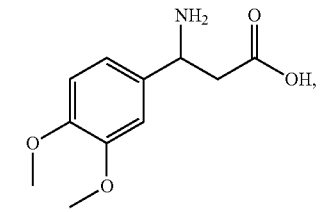
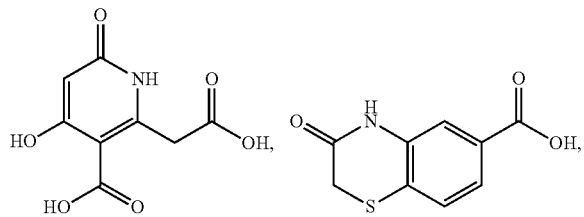
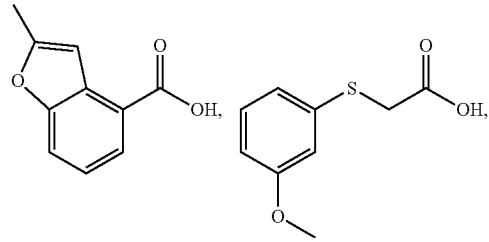
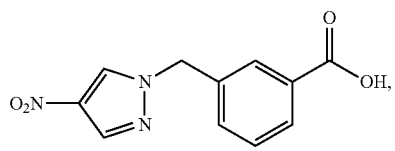
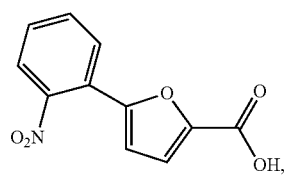
-continued
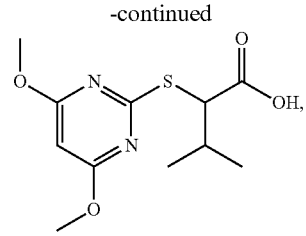
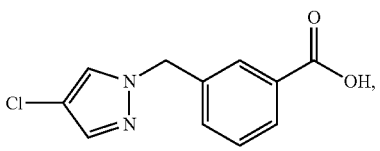
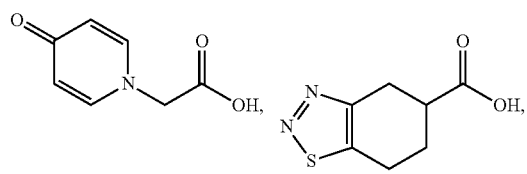
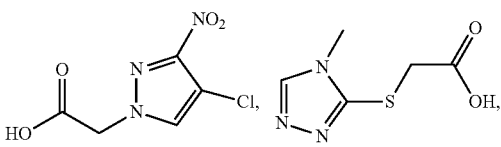
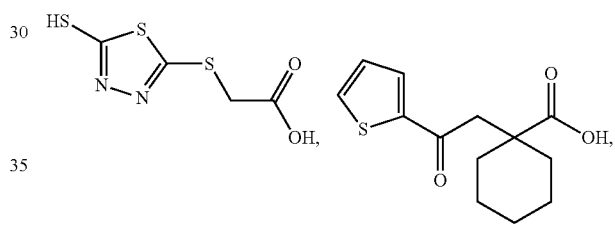
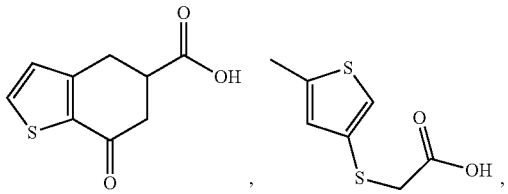
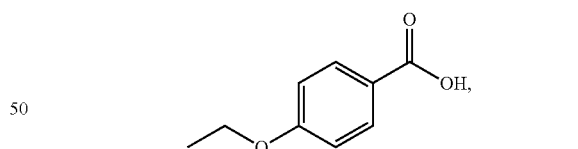
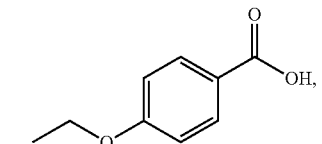
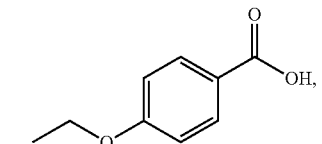
as well as racemates and isolated enantiomers and diastereomers thereof.
In another embodiment, the present invention pertains, at least in part, to methods for treating or preventing a blood disorder in a subject by administering to the subject an effective amount of a compound of formula III:

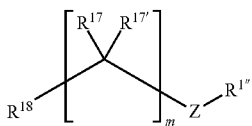

(III)

wherein
R$^{1''}$ is hydroxy or alkoxy;
Z is C(S), SO, SO$_2$ or PO$_2$;
m is 0 or an integer from 1-5;
R$^{17}$ and R$^{17'}$ are each independently hydrogen, alkyl, halogen, hydroxyl, thiol, alkenyl, alkynyl, aryl, acyl, alkoxy, amino, alkylamino or heterocyclic;
R$^{18}$ is hydrogen, alkyl, cycloalkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, heteroaryl, hydroxyl or halogen;
and racemates, isolated enantiomers or diastereomers, and pharmaceutically acceptable salts thereof.

In one embodiment, R$^{1''}$ is hydroxyl, Z is SO$_2$, m is 0, and R$^{18}$ is disubstituted aryl substituted by, for example, nitro and fluoro.

In yet another embodiment, the present invention pertains, at least in part, to methods for treating or preventing a blood disorder in a subject by administering to the subject an effective amount of a compound of formula III, wherein the compound of formula III is:

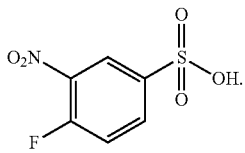 [SMILES: O=[N+]([O-])c1cc(S(=O)(=O)O)ccc1F]

In another embodiment, the present invention pertains, at least in part, to methods for treating or preventing a blood disorder in a subject by administering to the subject an effective amount of a compound of formula:

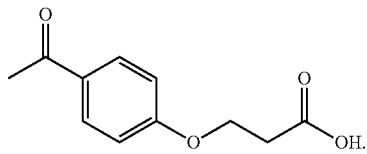

In yet another embodiment, the invention pertains, at least in part, to a compound of formula I:

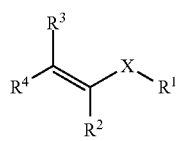

(I)

wherein
R$^1$ is hydroxy or alkoxy;
X is C(O), C(S), SO, SO$_2$ or PO$_2$;

R$^2$ and R$^3$ are each independently hydrogen, alkyl, halogen, hydroxyl, thiol, alkenyl, alkynyl, aryl, acyl, alkoxy, amino, alkylamino or heterocyclic;
R$^4$ is alkyl, cycloalkyl, alkenyl, alkynyl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, heteroaryl, halogen or

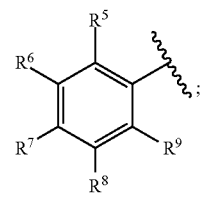

R$^5$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to R$^6$ to form a ring;
R$^6$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to R$^5$ or R$^7$ to form a ring;
R$^7$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to R$^6$ or R$^8$ to form a ring;
R$^8$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to R$^7$ or R$^9$ to form a ring;
R$^9$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, nitro, halogen or optionally linked to R$^8$ to form a ring;
and racemates, isolated enantiomers or diastereomers, and pharmaceutically acceptable salts thereof;
provided that when R$^4$ is

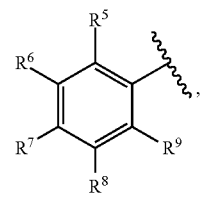

R$^5$, R$^6$, R$^7$, R$^8$, and R$^9$ are each not hydrogen; and when R$^6$, R$^7$, R$^8$, and R$^9$ are each hydrogen, R$^5$ is not methoxy; and when R$^5$, R$^7$, R$^8$, R$^9$ are hydrogen, R$^6$ is not methoxy; and when R$^5$, R$^8$ and R$^9$ are hydrogen, R$^6$ and R$^7$ are not methoxy;

provided that the compound is not a compound of the formula:

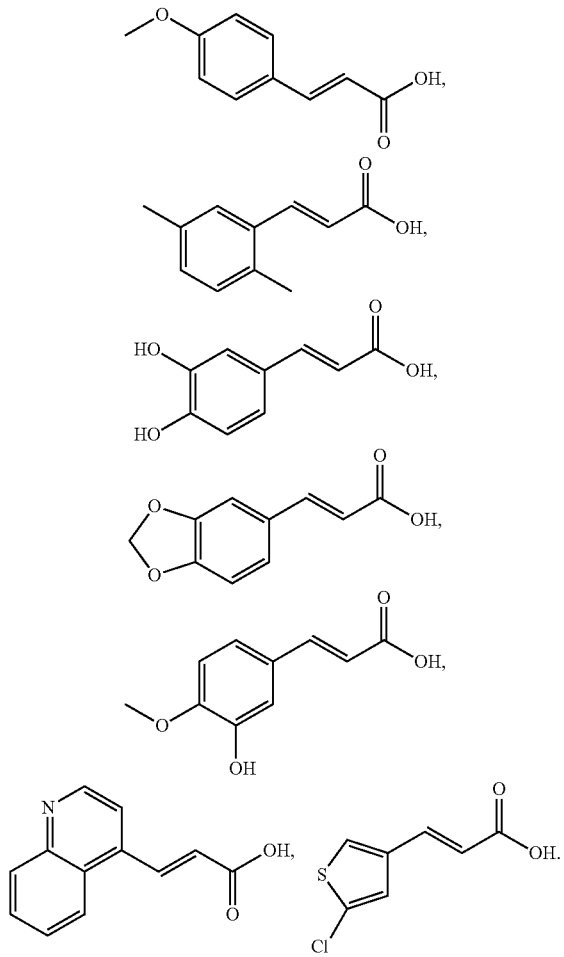

The present invention also pertains, at least in part, to a compound of formula II:

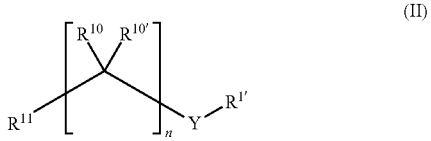

wherein
R$^{1'}$ is hydroxy or alkoxy;
Y is C(O);
n is 0 or an integer from 1 to 5;
R$^{10}$ and R$^{10'}$ are each independently hydrogen, alkyl, halogen, hydroxyl, thiol, alkenyl, alkynyl, aryl, acyl, alkoxy, amino, alkylamino, heterocyclic or optionally joined to form a ring;
R$^{11}$ is CR$^{11'}$R$^{11''}$R$^{11'''}$, alkenyl, cycloalkyl, alkynyl, arylalkyl, amido, alkylamino, amino, arylamino, carbonylalkyl, alkylcarbonyl, arylcarbonyl, alkylaminocarbonyl, alkoxycarbonyl, alkylcarbonyloxy, alkyloxycarbonyloxy, arylcarbonyloxy, thiol, alkylthio, arylthio, alkenyl, heterocyclic, heteroaryl, hydroxy, halogen or

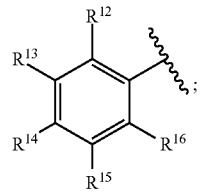

R$^{11'}$ and R$^{11''}$ are each independently hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxyl, halogen or R$^{11'}$ and R$^{11''}$ are optionally joined to form a ring;
R$^{11'''}$ is alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy or halogen;
R$^{12}$ is hydrogen, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic or optionally linked to R$^{13}$ to form a ring;
R$^{13}$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy or optionally linked to R$^{12}$ or R$^{14}$ to form a ring;
R$^{14}$ is hydrogen, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, halogen or optionally linked to R$^{13}$ or R$^{15}$ to form a ring;
R$^{15}$ is hydrogen, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, halogen or optionally linked to R$^{14}$ or R$^{16}$ to form a ring;
R$^{16}$ is hydrogen, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, halogen or optionally linked to R$^{15}$ to form a ring;
and racemates, isolated enantiomers or diastereomers, and pharmaceutically acceptable salts thereof;
provided that when R$^{11}$ is

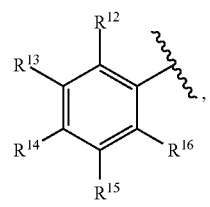

$R^{12}$, $R^{13}$, $R^{14}$, $R^{15}$, and $R^{16}$ are each not hydrogen; and provided when n is 2, $R^{11}$ is
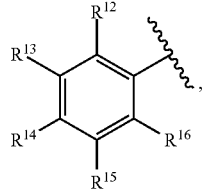
and $R^{10}$, $R^{10'}$, $R^{12}$, $R^{15}$, and $R^{16}$ are hydrogen, then $R^{14}$ and $R^{15}$ are not methoxy; and provided when n is 1, $R^{11}$ is
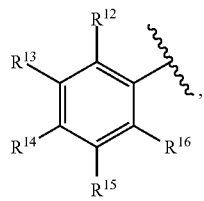
and $R^{10}$, $R^{10'}$, $R^{13}$, $R^{14}$, and $R^{16}$ are hydrogen, then $R^{12}$ and $R^{15}$ are not methoxy;
and provided that the compound is not a compound of:
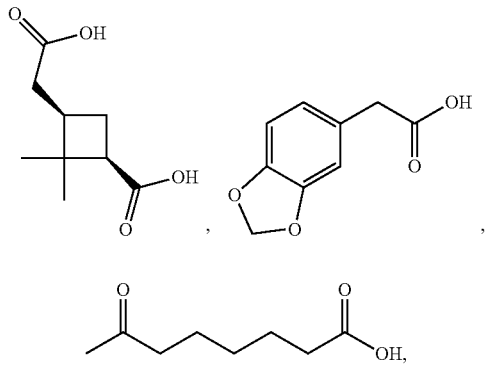
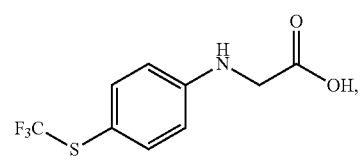
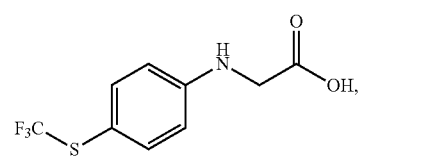
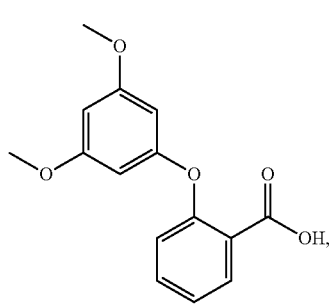
-continued
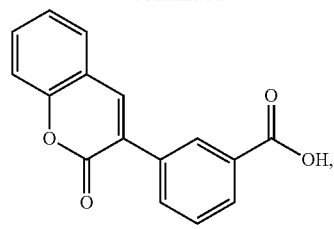
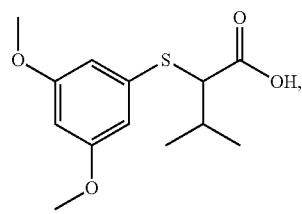
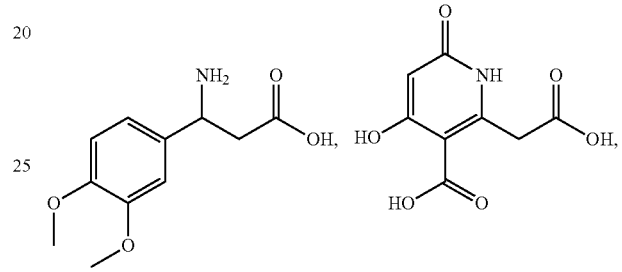
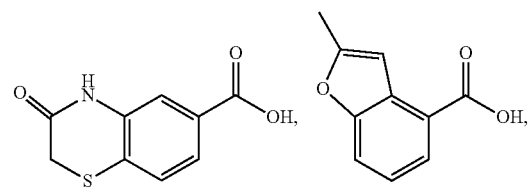
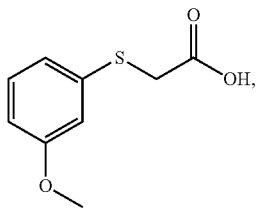
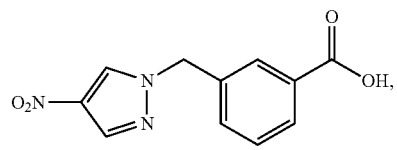
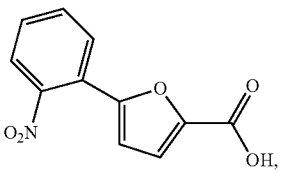
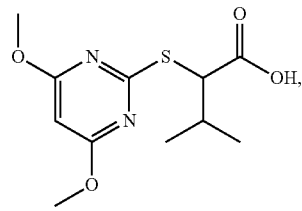

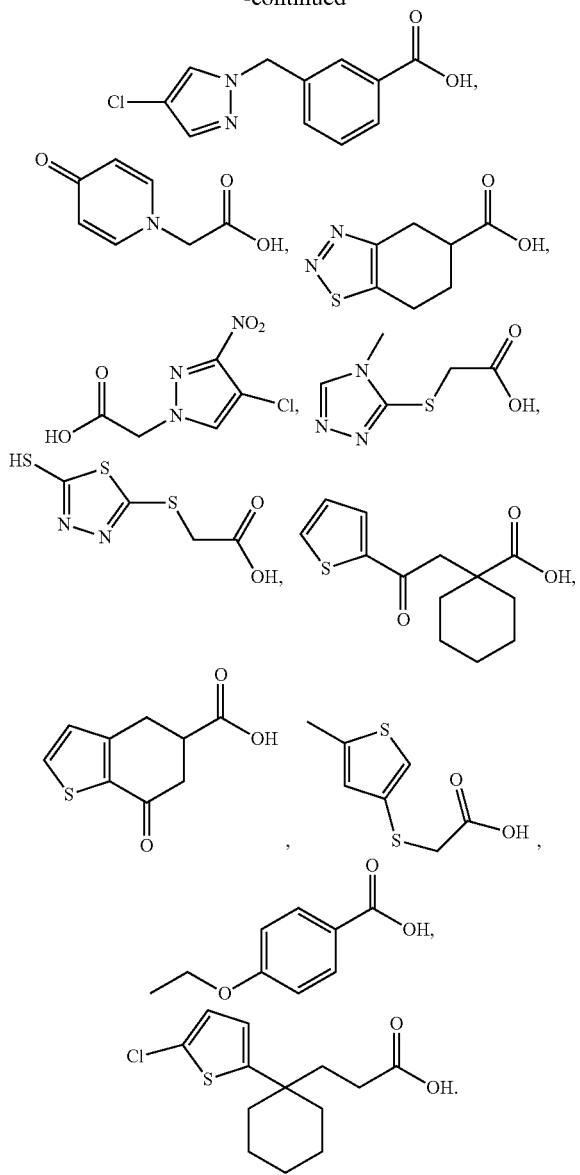

In a further embodiment, the present invention pertains, at least in part, to a compound of formula III:

$$\text{(III)}$$

wherein
R$^{1''}$ is hydroxy or alkoxy;
Z is C(S), SO, SO$_2$ or PO$_2$;
m is 0 or an integer from 1-5;
R$^{17}$ and R$^{17'}$ are each independently hydrogen, alkyl, halogen, hydroxyl, thiol, alkenyl, alkynyl, aryl, acyl, alkoxy, amino, alkylamino or heterocyclic;
R$^{18}$ is hydrogen, alkyl, cycloalkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, heteroaryl, hydroxyl or halogen;
and racemates, isolated enantiomers or diastereomers, and pharmaceutically acceptable salts thereof;
provided that the compound is not:

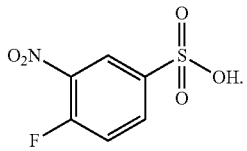 [SMILES: O=[N+]([O-])c1cc(S(=O)(=O)O)ccc1F]

In one embodiment, the compounds of the invention do not include the compounds described in S. Casteneda et al., *Blood Cells, Molecules, and Diseases,* 35 (2005) 217-226.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., C$_1$-C$_6$ for straight chain, C$_3$-C$_6$ for branched chain), and more preferably 4 or fewer. Likewise, preferred cycloalkyls have from 3-8 carbon atoms in their ring structure, and more preferably have 5 or 6 carbons in the ring structure. The term C$_1$-C$_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl(benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxophenyl, quinoline, isoquinoline, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl(alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" or "alkyl aminoalkyl" refers to an alkyl, alkenyl, or alkynyl group bound to a nitrogen atom which is also bound to an alkyl group.

The term "amide" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "ring" means cycloalkyl or aryl as these terms are used and defined herein.

The term "prodrug moiety" includes moieties which can be metabolized in vivo and moieties which may advantageously remain esterified or otherwise protected in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

It will be noted that the structure of some of the compounds of this invention includes asymmetric carbon atoms, and thus may exist as racemic mixtures or as isolated isomeric forms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The present invention pertains, at least in part, to methods for treating a blood disorder in a subject by administering to the subject an effective amount of a compound of the invention (e.g., a compound of Formula I, II, III or otherwise described herein, including isolated enantiomers or diastereomers).

The term "treating" includes curing as well as ameliorating at least one symptom of the state, disease or disorder, e.g., the blood disorder. Therefore, prevention of blood disorders or at least one symptom thereof is also contemplated herein.

The term "blood disorder" includes disorders which can be treated, prevented, or otherwise ameliorated by the administration of a compound of the invention, e.g., a compound of formula I, II, III or otherwise described herein). A blood disorder is any disorder of the blood and blood-forming organs. The term blood disorder includes nutritional anemias (e.g., iron deficiency anemia, sideropenic dysphasia, Plummer-Vinson syndrome, vitamin $B_{12}$ deficiency anemia, vitamin $B_{12}$ deficiency anemia due to intrinsic factor, pernicious anemia, folate deficiency anemia, and other nutritional anemias), myelodysplastic syndrome, bone marrow failure or anemia resulting from chemotherapy, radiation or other agents or therapies, hemolytic anemias (e.g., anemia due to enzyme disorders, anemia due to phosphate dehydrogenase (G6PD) deficiency, favism, anemia due to disorders of glutathione metabolism, anemia due to disorders of glycolytic enzymes, anemias due to disorders of nucleotide metabolism and anemias due to unspecified enzyme disorder), thalassemia (α-thalassemia, β-thalassemia, δβ-thalassemia, thalassemia trait, hereditary persistence of fetal hemoglobin (HPFP), and unspecified thalassemias), sickle cell disorders (sickle cell anemia with crisis, sickle cell anemia without crisis, double heterozygous sickling disorders, sickle cell trait and other sickle cell disorders), hereditary hemolytic anemias (hereditary spherocytosis, hereditary elliptocytosis, other hemaglobinopathies and other specified hereditary hemolytic anemias, such as stomatocyctosis), acquired hemolytic anemia (e.g., drug-induced autoimmune hemolytic anemia, other autoimmune hemolytic anemias, such as warm autoimmune hemolytic anemia, drug-induced non-autoimmune hemolytic anemia, hemolytic-uremic syndrome, and other non-autoimmune hemolytic anemias, such as microangiopathic hemolytic anemia); aplastic anemias (e.g., acquired pure red cell aplasia (erythroblastopenia), other aplastic anemias, such as constitutional aplastic anemia and fanconi anemia, acute posthemorrhagic anemic, and anemias in chronic diseases), coagulation defects (e.g., disseminated intravascular coagulation (difibrination syndrome)), hereditary factor VIII deficiency (hemophilia A), hereditary factor IX deficiency (Christmas disease), and other coagulation defects such as Von Willebrand's disease, hereditary factor XI deficiency (hemophilia C), purpura (e.g., qualitative platelet defects and Glanzmann's disease), neutropenia, agranulocytosis, functional disorders of polymorphonuclear neutrophils, other disorders of white blood cells (e.g., eosinophilia, leukocytosis, lymophocytosis, lymphopenia, monocytosis, and plasmacyctosis), diseases of the spleen, methemoglobinemia, other diseases of blood and blood forming organs (e.g., familial erythrocytosis, secondary polycythemia, essential thrombocytosis and basophilia), thrombocytopenia, infectious anemia, hypoproliferative or hypoplastic anemias, hemoglobin C, D and E disease, hemoglobin lepore disease, and HbH and HbS diseases, anemias due to blood loss, radiation therapy or chemotherapy, or thrombocytopenias and neutropenias due to radiation therapy or chemotherapy, sideroblastic anemias, myelophthisic anemias, antibody-mediated anemias, and certain diseases involving lymphoreticular tissue and reticulohistiocytic system (e.g., Langerhans' cell hystiocytosis, eosinophilic granuloma, Hand-Schüller-Christian disease, hemophagocytic lymphohistiocytosis, and infection-associated hemophagocytic syndrome).

In one embodiment, the compounds of formula I, II, III or otherwise described herein stimulate fetal hemoglobin production, hematopoiesis, erythropoiesis, myelopoiesis and/or neutrophil production upon administration to a subject for the treatment of a blood disorder.

In one embodiment, the compounds of formula I, II, III or otherwise described are administered to the subject for treatment of a blood disorder in combination with one or more cytokines. In one embodiment, the cytokine is selected from the group consisting of IL-3, GM-CSF, G-CSF, stem cell factor (SCF) and IL-6.

In the therapeutic methods of the invention, one or more compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

In another embodiment, the invention pertains, at least in part to a pharmaceutical composition of an effective amount of a compound of formula I, formula II, formula III, or

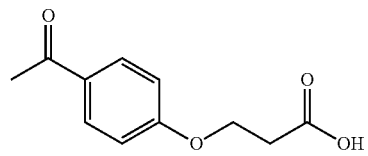

and racemates, isolated enantiomers or diastereomers thereof, and a pharmaceutically acceptable carrier.

The language "pharmaceutically acceptable carrier" includes substances capable of being coadministered with the compound(s) of the invention and which allow both to perform their intended function, e.g., treat or prevent a blood disorder. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The compounds of the invention that are basic in nature are capable of forming a wide variety of salts with various inorganic and organic acids. The acids that may be used to prepare pharmaceutically acceptable acid addition salts of the compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other compounds of the invention not specifically described in the foregoing experimental section can be accomplished using combinations of the reactions described above that will be apparent to those skilled in the art.

The compounds of the invention that are acidic in nature are capable of forming a wide variety of base salts. The chemical bases that may be used as reagents to prepare pharmaceutically acceptable base salts of those compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of compounds of the invention that are acidic in nature may be formed with pharmaceutically acceptable cations by conventional methods. Thus, these salts may be readily prepared by treating the compound of the invention with an aqueous solution of the desired pharmaceutically acceptable cation and evaporating the resulting solution to dryness, preferably under reduced pressure. Alternatively, a lower alkyl alcohol solution of the compound of the invention may be mixed with an alkoxide of the desired metal and the solution subsequently evaporated to dryness.

The compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating blood disorders in a subject, e.g., a mammal. Preferred mammals include cats, dogs, pigs, rats, mice, monkeys, chimpanzees, baboons and humans. In one embodiment, the subject is suffering from a blood disorder. In another embodiment, the subject is at risk of suffering from a blood disorder.

The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating blood disorders can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is derivatized with differentially degradable coatings, e.g., by microencapsulation, multiple coatings, etc.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior therapies. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of the compounds of the invention generally to ensure their efficacy under normal use circumstances. Especially when employed for therapeutic treatment of humans and animals in vivo, the practitioner should take all sensible precautions to avoid conventionally known contradictions and toxic effects.

Furthermore, the invention also pertains to the use of a compound of formula I, II, III or a compound otherwise described herein for the preparation of a medicament. The medicament may include a pharmaceutically acceptable carrier and the compound is an effective amount, e.g., an effective amount to treat a blood disorder.

EXEMPLIFICATION OF THE INVENTION

Example 1

Identification of Small Molecule Inducers of Fetal Hemoglobin

Small molecule inducers of fetal hemoglobin were identified using computer modeling techniques.

The pharmacophore was constructed with the TFIT module of the FLO molecular modeling software. It was assumed that the carboxylic acids would bind to the receptor in an analogous fashion, and therefore, the superposition of the carboxylic oxygens was biased by imposing a 5 kJ superimposition energy constraint. Five hundred iterations of TFIT were used in the calculations.

TFIT produced an ensemble of low energy superimposition. The superimposition with the tightest overlay was taken to be the initial pharmacophore template. This pharmacophore was tested to see if it could distinguish between active and inactive compounds. TFIT was first used to determine the best match between the pharmacophore and four compounds which had been identified as inactive in the β/γ-globin promoter driven reporter gene assay in previous studies.

The TFIT was next used to determine how well five additional compounds, which were active in the β/γ-globin promoter driven reporter gene assay would match the template. The template was used to design and select new compounds for testing. Compounds were selected from available compound data bases and evaluated by fitting them onto the template with TFIT.

The compounds generated from the modelling were tested in the β/γ-globin promoter driven reporter gene assay and were found to have statistically significant activity in the assay (Table 1). All of the compounds shown in Table 1 had a % γ globin promoter induction (above untreated control) of between about 100%-200%.

TABLE 1

| Compound Code | Structure |
|---|---|
| A | [structure: 4-methoxycinnamic acid] |
| B | [structure: 2,5-dimethylcinnamic acid] |
| C | [structure: 3,4-dihydroxycinnamic acid (caffeic acid)] |

TABLE 1-continued

| Compound Code | Structure |
|---|---|
| D | (3,4-methylenedioxy)cinnamic acid structure |
| E | 4-methoxy-3-hydroxycinnamic acid structure |
| H | 2,2-dimethylcyclobutane dicarboxylic acid derivative structure |
| I | (3,4-methylenedioxyphenyl)acetic acid structure |
| J | 6-oxoheptanoic acid structure |

Next, a "pseudo" receptor was constructed around the pharmacophore by refining the original pharmacophore template. A new template was constructed by adding two of the most active new compounds. The compounds were selected primarily for the additional structural information that they contained.

The "pseudo" binding site was construction using FLO. This "pseudo" binding site was composed of functional groups selected to form hydrogen bonds with the ligands, and functional groups that would mimic the hydrophobic surface of the binding site. A guanidinium group was selected form hydrogen bonds with the acidic groups of the ligands. A pyrrole group was used to mimic the binding site hydrogen bond donors. These groups were positioned around the template molecules and anchored to the chemically complimentary ligand atoms with a 10 kJ constraint. The "pseudo" program of FLO automatically filled the remaining volume with propane to mimic the binding site's hydrophobic surface. This structure was next subject to several rounds of dynamics.

Once the template atoms were removed, the shell of propanes, the pyrrole group and the guanidinium groups represented the receptor binding site. To ensure a moderate amount of binding site flexibility, the atoms of the binding site were allowed to move with a molecular mechanics force field and an additional flat well constraint [radius 0.5 Å, quadratic penalty 20 kJ/Å$^2$] was imposed.

To test the "pseudo" binding site, twenty compounds (14 active and 6 inactive in the β/γ-globin promoter driven reporter gene assay) were docked into the binding site model using the docking module SDOCK+ of FLO+. For each docked conformation, FLO+ computed a predicted binding free energy using an empirical scoring function consisting of contact energy, hydrogen bonding energy, polar desolvation, bumping, internal energy and entropy. For the most active compounds, the predicted free energy (reported as pI or the $-\log K_i$), fell between 6.6 and 6.9, with hydrogen bonding energies between 7.4 and 8.9 kJ/mol. The pI values for the four inactive compounds ranged from 5.6 to 6.2 with hydrogen bonding energies between 5.6 and 7.0 kJ/mol. A combination of the pI and the hydrogen bonding energy was used to distinguish between active and inactive compounds.

Compounds for screening were then selected from a database of 13,000 commercially available compounds. Only molecules with an acid group and less that 24 heavy atoms were chosen, resulting in 630 compounds. These compounds were docked into the binding site using SDOCK+. The binding modes were scored using FLO+ and the best 10 conformations for each compound were retained for visual inspection.

Using the pI and hydrogen bonding energy as criteria, 30 compounds were selected for in vitro testing. The scores for these compounds ranged for pI 5.1 (hydrogen bonding energy of −8.1 kJ/mol) to pI 8.8 (hydrogen bonding of 9.4 kJ/mol). Twenty six of these compounds were acquired and tested. Table 2 shows the results of the β/γ-globin promoter driven reporter gene assay for the twenty-six compounds. '*' indicates a 80-100% increase; '' indicates a 100%-200% increase; and '*' indicates an over 200% increase of γ globin promoter induction over untreated controls.

TABLE 2

| Compound Code | Structure | % γ globin promoter induction (above untreated control) |
|---|---|---|
| F | quinoline-4-acrylic acid structure | *** |
| K | 2-hydroxybenzylidene thiazolidine-2,4-dione N-acetic acid structure | * |
| M | quinazolin-4-ylamino butyric acid structure | ** |

TABLE 2-continued

| Compound Code | Structure | % γ globin promoter induction (above untreated control) |
|---|---|---|
| N | 4-(trifluoromethylthio)phenyl glycine | *** |
| O | 2-(3,5-dimethoxyphenoxy)benzoic acid | * |
| P | 3-(2-oxo-2H-chromen-3-yl)benzoic acid | *** |
| Q | 2-((3,5-dimethoxyphenyl)thio)-3-methylbutanoic acid | ** |
| R | 3-amino-3-(3,4-dimethoxyphenyl)propanoic acid | *** |
| S | 5-carboxy-4-hydroxy-6-oxo-1,6-dihydropyridin-2-yl acetic acid | ** |
| T | 3-oxo-3,4-dihydro-2H-benzo[b][1,4]thiazine-6-carboxylic acid | ** |
| V | 2-((3-methoxyphenyl)thio)acetic acid | ** |
| W | 3-((4-nitro-1H-pyrazol-1-yl)methyl)benzoic acid | ** |
| X | 5-(2-nitrophenyl)furan-2-carboxylic acid | ** |
| Y | 2-((4,6-dimethoxypyrimidin-2-yl)thio)-3-methylbutanoic acid | ** |
| Z | 3-((4-chloro-1H-pyrazol-1-yl)methyl)benzoic acid | ** |
| AA | 2-(4-oxopyridin-1(4H)-yl)acetic acid | ** |
| AB | 4,5,6,7-tetrahydrobenzo[d][1,2,3]thiadiazole-5-carboxylic acid | ** |

TABLE 2-continued

| Compound Code | Structure | % γ globin promoter induction (above untreated control) |
|---|---|---|
| AC | (structure: pyrazole with NO2, Cl, and N-CH2-COOH) | ** |
| AD | (structure: 4-methyl-triazole-thio-acetic acid) | ** |
| AE | (structure: thiadiazole with SH and S-CH2-COOH) | ** |
| AF | (structure: thiophene-CO-CH2-cyclohexane-COOH) | * |
| AG | (structure: 4-oxo-tetrahydrobenzothiophene-carboxylic acid) | ** |
| AH | (structure: 5-methylthiophene-S-CH2-COOH) | ** |
| AI | (structure: 4-ethoxybenzoic acid) | ** |
| AJ | (structure: 5-chlorothiophene-cyclohexane-propionic acid) | ** |
| AK | (structure: 3-nitro-4-fluorobenzenesulfonic acid) | ** |

Example 2

In Vitro Stimulation of Fetal Globin mRNA Expression

This example demonstrates that the test compounds predicted to be active by reporter gene assays and molecular modeling produce a significant increase in fetal (gamma) globin mRNA in cells cultured in vitro. Furthermore, the concentrations required were significantly lower (5-40 micromolar) than concentrations required for prior generation inducers (100-200 micromolar), making these compounds more suitable for therapeutic and pharmacologic compositions γ-globin mRNA was analyzed in control and treated erythroid colonies cultured from cord blood, by RT-PCR.

Induction (increase) in fetal globin mRNA compared to untreated control levels with each compound is shown in Table 3 below. The R enantiomer of compound Y demonstrated fetal globin inducing action, whereas the S enantiomer did not induce fetal globin in 2 of (the same) 3 cultures.

TABLE 3

Increase in Fetal Globin mRNA

| Compound | Concentration required, micromolar | Mean change above control, % | No. of Positive responses |
|---|---|---|---|
| M | 5 | 70 | 4/6 |
| P | 20 | 86 | 6/6 |
| 2-methyl-1-benzofuran-4-carboxylic acid | 5 | 46 | 6/6 |
| V | 5 | 50 | 6/6 |
| W | 40 | 368 | 5/6 |
| 3-(5-chlorothien-3-yl)acrylic acid | 30 | 50 | |
| Y racemic mix | 5 | 20 | 1/3 |
| Y + R | 5 | 67 | 2/3 |
| Y − S | 5 | −2 | 1/3 |

These levels of fetal globin induction are higher than the induction by previously reporter inducing agents, and occur at lower concentrations, i.e., these agents have higher potency.

In a related study, the relative luciferase reporter gene induction, γ-globin gene induction, and F cell production was tested for several of the candidate compounds. The relative in vitro γ-globin gene reporter stimulation for the tested compounds was as follows: compound P>M>W=R=Y. The relative in vitro γ-globin gene induction for the tested compounds was as follows: P>R=M>Y>W>. The relative in vitro F-cell production was as follows: W>Y>R>M>P. The relative potency for F-cell production was as follows: R>M>Y>P>W.

Example 3

Effects on Erythroid and Myeloid Cell Growth In Vitro

This example demonstrates that the test compounds predicted to be active by reporter gene assays and molecular modeling produce a significant increase in numbers of erythroid and myeloid colonies or proportion of cells expressing fetal globin in in vitro cultured cells from a variety of sources under a variety of culture conditions. Similar to other in vitro tests described herein, the concentrations required for these biological effects were significantly lower (5-40 micromolar) than concentrations required for prior generation inducers (100-200 micromolar), making these compounds more suitable for therapeutic and pharmacologic compositions.

Compounds predicted in the molecular model to be γ-globin inducers were evaluated in a series of assays for activity in 1) stimulating activity from the fetal globin gene promoter, (the action which can ameliorate sickle cell disease and beta thalassemia), and 2) for any effects on stimulating erythroid or myeloid cell growth and proliferation, the action which can treat blood cell deficiencies.

Erythroid burst-forming units (BFU-E) (erythroid progenitors) and colony-forming units granulocyte-macrophage (CFU-GM) (myeloid colonies) were cultured in semi-solid or in two-phase suspension media, with or without hematopoietic growth factors at high levels (e.g., erythropoietin at 3 U/ml) or reduced levels (BFU-E cell proliferation was evaluated by enumeration in colonies developing in the presence of reduced amounts of erythropoietin (0.5 U/ml) rather than 3 U (or 3000 mU)/ml, which is standard for these experimental systems), from cord blood or the peripheral blood of several types of humans. Experiments were carried out on samples derived from 1) β-thalassemia patients who expressed variable levels of fetal globin at baseline (and in untreated control cultures) and represent a variety of potential individual responses, 2) from normal umbilical cord blood samples, which express 40-50% fetal globin at baseline (and in untreated control cultures), 3) from CD34+ cells isolated from normal adult peripheral blood, which expressed low levels of fetal globin in untreated control cultures and at baseline; and 4) from peripheral blood of patients with sickle cell disease who were receiving treatment with hydroxyurea. These biological samples provide a range of potential difficulty in stimulating fetal globin expression in human patients.

Experiment 1

Hematopoietic colonies were enumerated with or without (+/−) the test compounds, and compared to colonies which developed in the presence of hematopoietic growth factors alone from the same subject (untreated control colonies), and proportions of cells expressing fetal globin (F-cells) were analyzed by FACScan analysis. The compounds M, N, P, R, T, 2-methyl-1-benzofuran-4-carboxylic acid, V, W, X, Y, Z, F and 3-(5-chlorothien-3-yl)acrylic acid, all resulted in significant increases in the proportion of F-cells above the percentage of F-cells in untreated controls, at the same low concentrations as required for fetal globin mRNA induction and increases in erythroid colony numbers with the compounds.

Experiment 2

Erythroid colonies were cultured from patients with beta thalassemia, either without any test compounds (Control), only an optimal panel of hematopoietic growth factors, or with one of the test compounds M, P, T, 2-methyl-1-benzofuran-4-carboxylic acid, V, W, X, Y, AK, AC, or AI. All of the listed test compounds increased the number of colonies as compared to the matched control cultures that were grown with an optimal panel of growth factors alone. Colony numbers were increased above the control cultures (% BFU-E/Control) by anywhere from 25% to 230%. Each of the listed test compounds was tested in at least 5 different patients' blood and the differences were statistically significant.

In a related study, BFU-E cultured from cord blood, was tested with or without compound M, P, R, T, W, Y, Z, AI, F, or 3-(5-chlorothien-3-yl)acrylic acid. The test compounds all induced increased numbers of colonies as compared to the controls. In this study the test compounds resulted in 50-250% more colonies than in control cultures from the same source.

Experiment 3

Representative novel compounds M, W, X, Y, and AI also stimulated production of myeloid colonies compared to control, untreated myeloid colonies from the same individual. Control colonies were established in cultures with no added growth factors to support myelopoiesis, in Iscove's Modified Dulbecco's Media (IMDM) methylcellulose media with charcoal-absorbed fetal bovine serum, beta mercaptoethanol, BSA. A 30-75% increase in de novo myeloid colonies was observed in cord blood cultured with the novel compounds at the same concentrations as required for increases in erythroid colonies.

Experiment 4

Erythroid cells cultured from adult blood are low-HbF expressing and are the most difficult to alter with regard to globin expression. This experiment analyzed erythroid cells cultured from adult blood in the presence or absence of representative test compounds.

Erythroid cells were generated by culturing purified CD34+ cells in Flt-3 ligand, stem cell factor (SCF) and IL-3 for seven days followed by growth in EPO for 14 days. For treatment, cells were cultured as above in a T75 flask then split into multiple flasks on day 8 and treatment with the test compounds was begun. Compound P or other test compounds were diluted from stock solutions with the microliter volumes of stock added to each culture flask for final working concentrations. Cells were enumerated every two days by hemacytometer count. RNA was harvested from $10^6$ cells every two days using RNeasy Plus Mini Kit (Qiagen) and qRT-PCR performed using IQ SybrGreen Supermix on an Opticon Monitor instrument (MJ Research). Samples were assayed in triplicate and raw data from the instrument was analyzed using a method suggested by Larionov et al. with beta-actin and G3PD assayed as controls (housekeeping genes). Separation of hemoglobins was performed by cation exchange HPLC using a 35×4.6 mm; 3 mm PolyCAT A column (Nest Group) as described previously by Cheryl Rognerud and Ching-Nan Ou, and outlined by the column manufacturer.

QPCR primers were designed using known sequences for α-globin, β-globin, γ-globin, β-actin and B3PD. Primers were designed to span at least one exon.

The results showed that erythroid cells peaked at day 12-14 of the erythroid phase. Cell counts were increased with 20 microM compound P as compared to control cells cultured with erythropoietin alone. Comparison of compound P at different doses showed that there was no effect on production/expression of alpha globin, but there was a reciprocal decrease in production of beta globin concomitantly with increases in fetal globin mRNA expression at the same doses. The activity was specific for inducing gamma (fetal) globin with reciprocal decrease in beta globin. Hemoglobin F protein levels increased in a compound P dose-dependent manner with a 19-fold increase in expression of fetal globin produced at 100 micromolar compound P as compared to untreated control cultures from the same subject with just one cycle of erythroid differentiation.

Experiment 5

In an additional study, comparative growth of erythroid (red blood cell) colonies cultured from cord blood samples was evaluated with the addition of growth factors alone or with the addition of test compounds.

Comparative growth of erythroid colonies cultured from cord blood samples under conditions with standard growth factors alone (Control), or with addition of test compounds or arginine butyrate (AB) (AB results in reduced colony numbers). Control and test cultures were established from the same samples with the same growth factors (EPO and Il-3) with addition of test compounds. The compounds tested were M, P, R, T, W, Y, Z, AI, F and 3-(5-chlorothien-3-yl)acrylic acid. Two compounds previously shown as positive proliferative agents were included for comparison. All compounds tested, except compound AI and 3-(5-chlorothien-3-yl) acrylic acid, resulted in an increase in red blood cell colony numbers by at least 25% above control numbers and was statistically significant. These results indicate that the test compounds stimulate red blood cell production even in conditions of maximal growth factors and in the absence of anemia.

Experiment 6

Erythroid colonies from the peripheral blood of 4 patients with sickle cell disease who were receiving treatment with Hydroxyurea (HU), a chemotherapeutic agent which suppresses marrow growth and reduces red blood cell production, were cultured alone or with added test compounds M, P, 2-methyl-1-benzofuran-4-carboxylic acid, V, W, Y (racemic mixture) or AI. L-arginine was added as a neutral control, and had no effect on numbers of erythroid colonies. Addition of arginine butyrate (AB), phenylacetate (PA), and hydroxyurea (HU) resulted in decreased numbers of erythroid colonies compared to control conditions.

As summarized in Table 5 below, addition of the test compounds M, P, 2-methyl-1-benzofuran-4-carboxylic acid, V, W, Y (racemic mixture) or AI (at the concentrations shown in the Table 5) resulted in an increase in numbers of erythroid colonies of at least 25% above control conditions. Compounds marked with a * are significantly different. 2-methyl-1-benzofuran-4-carboxylic acid and compound V require additional samples for statistical evaluation, but had positive effects in 3/3 different patients' cultures. These findings indicate that the test compounds stimulate erythroid cell production particularly in conditions of anemia and bone marrow suppression.

TABLE 5

Erythroid Colony Growth from Sickle Cell Patients +/− Test Compounds
% Change from control conditions with growth factors alone

| Compound | Concentration, micromolar | % Change from Control | Number with effects/ No effect | P-value |
|---|---|---|---|---|
| L-arginine (neutral control) | 150 | −3 | 3/5 | 0.6, not significant |
| AB (arginine butyrate) | 100 | −29 | 5/6 | 0.019 |
| PA Phenylacetate | 100 | −10 | 5/7 | 0.2 |
| M* | 1 | +58 | 5/5 | 0.035 |
| P* | 100 | +32 | 7/7 | 0.016 |
| 2-methyl-1-benzofuran-4-carboxylic acid | 10 | +51 | 3/3 | 0.1 |
| V | 10 | +35 | 3/3 | 0.09 |
| W* | 40 | +47 | 5/5 | 0.048 |
| Y racemic mix* | 50 | +47 | 6/7 | 0.024 |
| AI* | 30 | +51 | 4/5 | 0.04 |
| Hydroxyurea | 20 | −33 | 2/2 | 0.58 |

Table 2

In summary, the experiments described in this example show that representative test compounds produce a significant increase in numbers of erythroid and myeloid colonies or proportion of cells expressing fetal globin in in vitro cultured cells derived from a variety of sources under culture conditions relevant to blood conditions including anemia, sickle cell anemia and beta thalassamia.

Example 4

In Vivo Efficacy in a Non-Human Primate Model

Compounds P, Y and W were evaluated in a non-human primate model to evaluate functional activity of these candidate compounds in stimulating either fetal globin expression or production of blood cells. As described below, these studies demonstrated potent in vivo activity of the compounds for inducing fetal globin expression and production of blood cells.

Juvenile baboons were catheterized with venous and arterial catheters, and were phlebotomized a set amount of blood daily to maintain anemia with a hemoglobin level of 7.0-7.5 g/dl, from a baseline normal hemoglobin level of (12-13 g/dl). Normal saline was infused to replace the amount of blood withdrawn. This degree of phlebotomy exchanges the blood volume every 10-20 days.

Fetal globin mRNA was analyzed at baseline anemia before and following administration of test compounds. Globin chain protein synthesis confirmed the mRNA findings.

Following establishment of the stable level of anemia, a test compound was administered once/day, either intravenously or orally, and blood was withdrawn through the arterial catheter for analysis of globin mRNA or for analysis of the test compound in the plasma by HPLC-MS. Pharmacokinetic profiles were established from the plasma levels and oral bioavailability (comparing area under the curve between IV and oral plasma levels) was determined for the test compounds.

Pharmacokinetic profiles of compounds M (100 mg/kg), P (25 mg/kg), 2-methyl-1-benzofuran-4-carboxylic acid (100 mg/kg), W (100 mg/kg), and Y (10 mg/kg) indicated that these compounds persist well above therapeutic levels for >8 hours after tolerable single oral doses. Human equivalent doses are 20-50% of doses in baboons. Unusually low doses of compound P (25 mg/kg) and of compound Y (10 mg/kg), respectively, were required. Previously reported compounds typically require 100-500 mg/kg/dose for induction of fetal globin. Compound Y in particular also does not produce an undesirable high initial burst level and persists for greater than 24 hours. The human equivalent doses are 10-20% of the baboon dose. Thus for compound Y, the human equivalent dose would be 1-2 mg/kg, a dose highly favorable for a pharmaceutical composition.

Compound P and compound Y treatment in anemic baboons induced 3 to 6-fold γ-globin mRNA expression. Prior generation compounds typically induce fetal globin mRNA only by 2-fold.

In a further in vivo study, compounds AK, Y and M were evaluated in a baboon and demonstrated significant increases in fetal globin expression at tolerable low doses. As shown in the previous Examples, these 3 compounds all stimulated erythroid cell proliferation in vitro and have favorable pharmacokinetic profiles after oral administration. The compounds were administered to an anemic baboon and studied for pharmacodynamic effects on induction of fetal globin, which is known to ameliorate the pathology of sickle cell anemia and beta thalassemia.

In anemic Baboon 5002, baseline fetal globin mRNA, assayed by RNAse protection, was 26% of non-alpha globin. With treatment with compound Y at 5 mg/kg/dose, fetal globin mRNA increased to 48% of non-alpha globin, an 85% increase over the baseline level. Treatment with compound AK at 50 mg/kg induced a 51% fetal globin mRNA increase, a 96% increase over the baseline level. Compound M treatment at 40 mg/kg induced a 67% fetal globin mRNA increase, a 257% increase over the baseline level. The human equivalent dose is 20% of these doses, or 1 mg/kg, 10 mg/kg, or 8 mg/kg respectively. Thus, these 3 compounds are highly suitable for pharmaceutical compositions at doses that human patients can readily tolerate.

In a related study, compound P was evaluated in a phlebotomized, anemic baboon showing no baseline expression of fetal globin and 100% of globin expression as beta globin. Treatment with compound P resulted in an induction of 7% fetal globin and a concomitant reduction in beta globin expression.

These findings show that these compounds are excellent candidates for treatment of the beta hemoglobinopathies and thalassemias.

Example 5

Induction of Fetal Globin Expression in an In Vivo Transgenic Mouse Model

This example demonstrates that compound W increases expression of human fetal globin mRNA expression and hematocrit in a transgenic mouse model.

Transgenic mice containing the human fetal globin gene and a micro-Locus Control Region (LCR) received no treatment (controls) or were treated with test compounds and γ-globin mRNA was analyzed by RT-PCR. Compound W was administered to mice transgenic for the micro-LCR-201 gamma-globin gene promoter, by IP injection once/day for 5 days/week for 2 weeks, and gamma-globin mRNA was assayed by qPCR. Hematocrit was analyzed once per week. A significant difference in expression of human fetal globin mRNA and in hematocrit between Control and compound W-treated mice was found in initial experiments as summarized in Table 4 below.

TABLE 4

| γ-Globin Induction by Compound W in Transgenic Mice | | |
|---|---|---|
| Study Treatment | γ-globin mRNA/S16 (mean relative units) | Hematocrit |
| None | 1508 | 51 +/− 0.45 |
| Compound W | 3418 | 57 +/− 3 |
| p-value, paired t-test | <0.05 | <0.05 |

Example 6

Synthesis of Compound Y Enantiomers

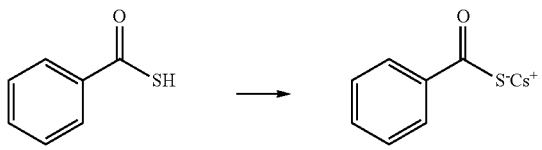

Cesium Thiobenzoate

To a solution of thiobenzoic acid (50.0 g, 361.8 mmol) in methanol (362 mL) was added $Cs_2CO_3$ (130 g, 398 mmol) in portions over 5 min. The resulting mixture was stirred 10 min until all solids were dissolved. The resulting solution was concentrated on the rotovap. The solid residue was diluted with 500 mL of acetone and the white solid ($CsHCO_3$) was filtered off. This process was repeated two times to ensure all $CsHCO_3$ was removed. The acetone was then concentrated to afford cesium thiobenzoate (Strijtveen, B.; Kellogg, R. M. *J. Org. Chem.* 1986, 51, 3664) as a yellow solid (81.5 g, 83%); $^1$H NMR (300 MHz, $CD_3OD$) δ 7.25-7.38 (m, 3H), 8.09 (dd, J=1.4, 8.2 Hz, 2H).

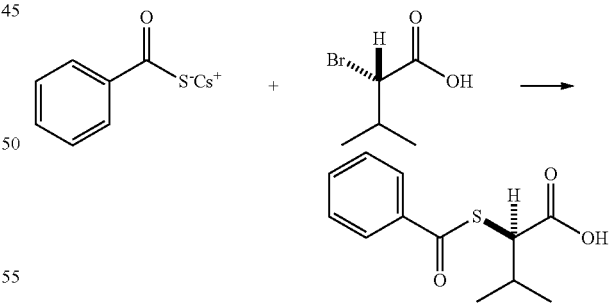

(R)-2-Benzoylthio-3-methylbutanoic acid

To a solution of (S)-(−)-2-bromo-3-methylbutyric acid (4.20 g, 23.2 mmol) in DMF (41 mL) was added cesium thiobenzoate (6.08 g, 22.5 mmol). The mixture was stirred at rt for 20 h. The resulting solution was diluted with ether (200 mL) and washed with $H_2O$ (4×40 mL). The ethereal layer was dried ($Na_2SO_4$), and concentrated. The crude residue was recrystallized from hexanes to afford (R)-2-benzoylthio-3- methylbutanoic acid as a pale yellow solid (4.05 g, 75%); $^1$H NMR (300 MHz, CDCl$_3$) δ 1.09 (d, J=7.4 Hz, 3H), 1.11 (d, J=7.4 Hz, 3H), 2.40 (m, 1H), 4.37 (d, J=5.9 Hz, 1H), 7.45 (t, J=7.4 Hz, 2H), 7.57 (t, J=7.4 Hz, 1H), 7.97 (d, J=7.4 Hz, 2H), 11.9 (br s, 1H); $^{13}$C NMR (75 MHz, CDCl$_3$) δ 19.8, 20.6, 30.5, 53.1, 127.6, 128.8, 133.9, 136.3, 177.9, 190.3; IR (neat) 3100, 2967, 1709, 1669 cm$^{-1}$; $[\alpha]_D^{22}$=+95.6 (c 1, CH$_2$Cl$_2$). All spectral data was identical to that previously published (Strijtveen, B.; Kellogg, R. M. *J. Org. Chem.* 1986, 51, 3664).

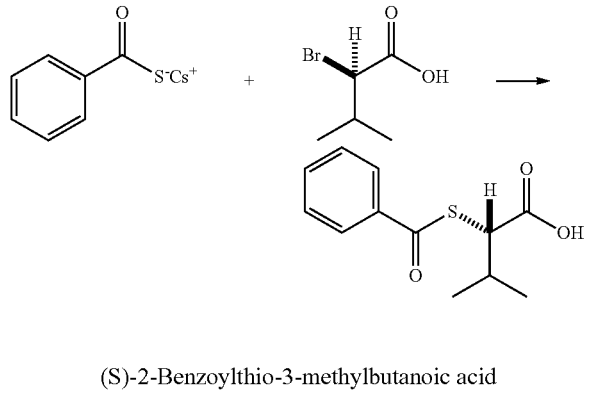

(S)-2-Benzoylthio-3-methylbutanoic acid

To a solution of (R)-(+)-2-bromo-3-methylbutyric acid (4.20 g, 23.2 mmol) in DMF (41 mL) was added cesium thiobenzoate (6.08 g, 22.5 mmol). The mixture was stirred at rt for 20 h. The resulting solution was diluted with ether (200 mL) and washed with H$_2$O (4×40 mL). The ethereal layer was dried (Na$_2$SO$_4$), and concentrated. The crude residue was recrystallized from hexanes to afford (S)-2-benzoylthio-3-methylbutanoic acid as a pale yellow solid (3.89 g, 72%); $^1$H NMR (300 MHz, CDCl$_3$) δ 1.09 (d, J=7.4 Hz, 3H), 1.11 (d, J=7.4 Hz, 3H), 2.40 (m, 1H), 4.37 (d, J=5.9 Hz, 1H), 7.45 (t, J=7.4 Hz, 2H), 7.57 (t, J=7.4 Hz, 1H), 7.97 (d, J=7.4 Hz, 2H), 12.0 (br s, 1H); $^{13}$C NMR (75 MHz, CDCl$_3$) δ 19.8, 20.6, 30.5, 53.1, 127.6, 128.8, 133.9, 136.3, 177.9, 190.3; IR (neat) 3100, 2967, 1709, 1669 cm$^{-1}$; $[\alpha]_D^{22}$=−94.2 (c 1, CH$_2$Cl$_2$).

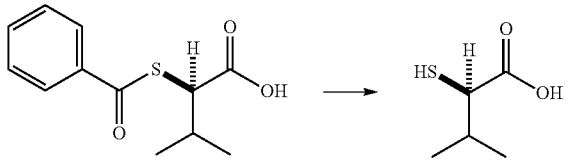

(R)-2-Mercapto-3-methylbutanoic acid

To a solution of (R)-2-benzoylthio-3-methylbutanoic acid (4.05 g, 17.0 mmol) in CH$_2$Cl$_2$ (68 mL) was added 3 M aqueous NH$_4$OH (68 mL). The mixture was stirred at rt for 3 h. The resulting solution was diluted with 2 M aqueous KOH (68 mL) and washed with CH$_2$Cl$_2$ (6×70 mL) to remove the benzamide. The aqueous layer was then acidified to pH 2 with concentrated aqueous HCl and extracted with CH$_2$Cl$_2$ (4×70 mL). The organic extracts were dried (Na$_2$SO$_4$) and concentrated to afford (R)-2-mercapto-3-methylbutanoic acid as a white solid (2.10 g, 92%); $^1$H NMR (300 MHz, CDCl$_3$) δ 1.05 (d, J=6.7 Hz, 3H), 1.09 (d, J=6.7 Hz, 3H), 1.96 (d, J=9.7 Hz, 1H), 2.07 (m, 1H), 3.13 (dd, J=8.1, 9.7 Hz, 1H); $^{13}$C NMR (75 MHz, CDCl$_3$) δ 19.3, 20.8, 32.6, 48.8, 179.8; IR (neat) 3100, 2966, 1705 cm$^{-1}$; $[\alpha]_D^{22}$=+41.0 (c 1, ether).

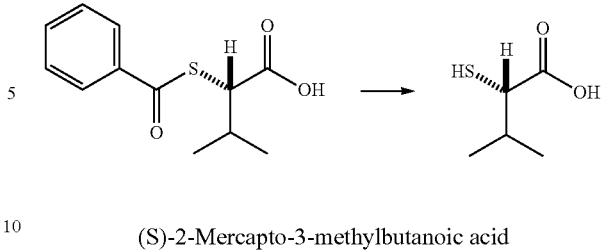

(S)-2-Mercapto-3-methylbutanoic acid

To a solution of (S)-2-benzoylthio-3-methylbutanoic acid (3.89 g, 16.3 mmol) in CH$_2$Cl$_2$ (65 mL) was added 3 M aqueous NH$_4$OH (65 mL). The mixture was stirred at rt for 3 h. The resulting solution was diluted with 2 M aqueous KOH (65 mL) and washed with CH$_2$Cl$_2$ (6×65 mL) to remove the benzamide. The aqueous layer was then acidified to pH 2 with concentrated aqueous HCl and extracted with CH$_2$Cl$_2$ (4×65 mL). The organic extracts were dried (Na$_2$SO$_4$) and concentrated to afford (S)-2-mercapto-3-methylbutanoic acid as a white solid (2.00 g, 91%); $^1$H NMR (300 MHz, CDCl$_3$) δ 1.05 (d, J=6.7 Hz, 3H), 1.09 (d, J=6.7 Hz, 3H), 1.96 (d, J=9.7 Hz, 1H), 2.07 (m, 1H), 3.13 (dd, J=8.1, 9.7 Hz, 1H); $^{13}$C NMR (75 MHz, CDCl$_3$) δ 19.3, 20.8, 32.6, 48.8, 179.8; IR (neat) 3100, 2966, 1705 cm$^{-1}$; $[\alpha]_D^{22}$=−40.2 (c 1, ether).

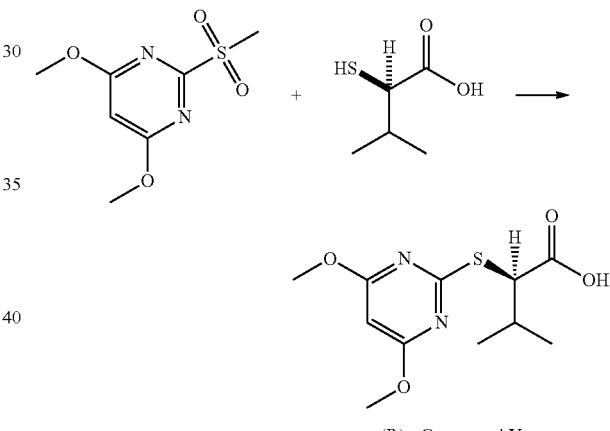

(R)-Compound Y

To (R)-2-mercapto-3-methylbutanoic acid (2.10 g, 15.6 mmol) was added aqueous NaOH (1.0 M in H$_2$O, 37.6 mL, 37.6 mmol). The mixture was stirred at rt for 10 min. The resulting solution was cooled to 0° C., diluted with DMF (20 mL), and 4,6-dimethoxy-2-(methylsulfonyl)pyrimidine (3.42 g, 15.6 mmol) in DMF (10 mL) was added (a slightly modified procedure of Fukuda, S.; Akiyoshi, Y.; Hori, K. *J. Org. Chem.* 1999, 64, 4768; 4,6-dimethoxy-2-(methylsulfonyl)pyrimidine is commercially available from Aldrich). The mixture was warmed to rt and stirred for 1 h. The resulting solution was quenched with 2 M HCl and extracted with ethyl acetate. The combined extracts were washed with brine, dried (Na$_2$SO$_4$) and concentrated. Purification by silica gel chromatography (gradient column, ethyl acetate-hexanes, 1:5→1:1→1:0) afforded (R)-compound Y as white crystals (3.77 g, 88%); $^1$H NMR (300 MHz, CDCl$_3$) δ 1.15 (d, J=6.4 Hz, 3H), 1.17 (J=6.4 Hz, 3H), 2.41 (m, 1H), 3.89 (s, 6H), 4.16 (d, J=5.9 Hz, 1H), 5.78 (s, 1H); $^{13}$C NMR (75 MHz, CDCl$_3$) δ 20.1, 20.9, 30.1, 54.4, 54.9, 86.5, 169.4, 170.9, 177.9; IR (neat) 3050, 2964, 1710, 1581, 1557 cm$^{-1}$; $[\alpha]_D^{22}$=+127.2 (c 1, CH$_2$Cl$_2$).

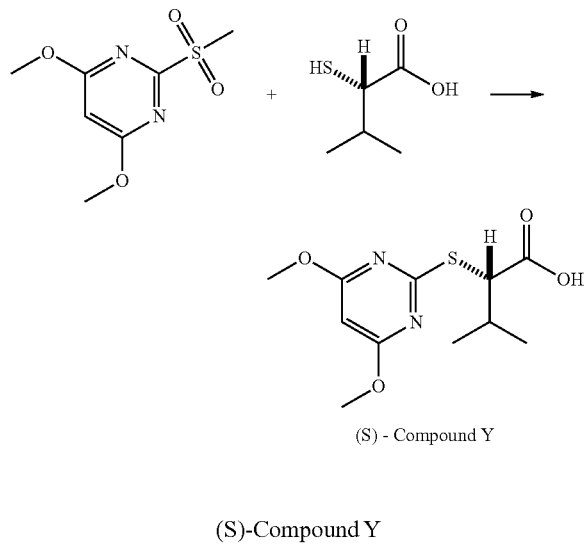

(S) - Compound Y (S)-Compound Y

To (S)-2-mercapto-3-methylbutanoic acid (2.00 g, 14.9 mmol) was added aqueous NaOH (1.0 M in H$_2$O, 35.8 mL, 35.8 mmol). The mixture was stirred at rt for 10 min. The resulting solution was cooled to 0° C., diluted with DMF (20 mL), and 4,6-dimethoxy-2-(methylsulfonyl)pyrimidine[2,3] (3.25 g, 14.9 mmol) in DMF (10 mL) was added. The mixture was warmed to rt and stirred for 1 h. The resulting solution was quenched with 2 M HCl and extracted with ethyl acetate. The combined extracts were washed with brine, dried (Na$_2$SO$_4$) and concentrated. Purification by silica gel chromatography (gradient column, ethyl acetate-hexanes, 1:5→1:1→1:0) afforded (S)-compound Y as white crystals (3.65 g, 90%); $^1$H NMR (300 MHz, CDCl$_3$) δ 1.15 (d, J=6.4 Hz, 3H), 1.17 (J=6.4 Hz, 3H), 2.41 (m, 1H), 3.89 (s, 6H), 4.16 (d, J=5.9 Hz, 1H), 5.78 (s, 1H); $^{13}$C NMR (75 MHz, CDCl$_3$) δ 20.1, 20.9, 30.1, 54.4, 54.9, 86.5, 169.4, 170.9, 177.9; IR (neat) 3050, 2964, 1710, 1581, 1557 cm$^{-1}$; $[\alpha]_D^{22}$=−127.3 (c 1, CH$_2$Cl$_2$).

Example 7

Selective Activity of the S Enantiomer of Compound Y

Compound Y exists naturally in a racemic mixture, and has the highly favorable PK properties described above. The experiments described herein demonstrate that the S enantiomer of compound Y stimulates erythroid cell proliferation significantly, while the R enantiomer does not stimulate cell proliferation. The R enantiomer of compound Y has activity in stimulating fetal globin expression (see Table 3).

The proliferative activity of compound Y—S enantiomer was tested in vitro in erythroid colonies cultured from peripheral blood of 3 sources of individuals: sickle cell anemia patients who were taking Hydroxyurea and have suppression of their endogenous erythropoiesis, a normal adult subject, and two cord blood samples. The erythroid cultures were established with low concentrations of Erythropoietin (0.5 U/ml) alone and with one or the other enantiomer of compound Y or the racemic mixture, or with high concentrations of EPO (3 Units/ml, =3000 mU/ml, 100-fold the normal physiologic concentration).

The cultures established in high EPO produced 25-45% (mean 35%) more colonies than the cultures established with the racemic mix in low EPO or the R enantiomer in low EPO. Addition of the S-enantiomer of compound Y at the same concentration resulted in a mean of 45% more erythroid colonies than in the racemic mixture (range 38-50%). Thus, the S enantiomer demonstrates the activity of stimulating proliferation of erythroid colonies in vitro.

Example 8

Molecular Mechanism of Action

Without being bound by theory, it is thought that the compounds described herein operate by a novel and highly specific molecular mechanism of action as elucidated further below.

The erythroid kruppel-like factor, EKLF, is an essential transcription factor for mammalian beta-like globin gene switch, and it specifically activates transcription of the adult beta-globin gene through binding of its zinc fingers to the promoter. It has been shown that transcription factor EKLF is required for activation of the gamma globin gene by the compounds described herein. EKLF was previously considered to activate primarily the beta (adult) globin gene. Transcription factor EKLF is actively recruited to the gamma-globin gene promoter by the compounds described herein. The human SWI/WNF complex is a ubiquitous multimeric complex that regulates gene expression by remodeling nucleosomal structure in an ATP-dependent manner. The SWI/SNF complex contains one of two core ATPases, BRG1 or BRM. These complexes can interact with sequence specific transcription factors to either promote or repress target gene activation, dependent on promoter context and complex content. The SWI/SNF complex chromatin-modifying core ATPase Brg1 is required for gamma globin induction by the compounds described herein. Brg1, the co-activator SWI/SNF complex chromatin-modifying ATPase, is actively recruited to the gamma-globin promoter by the compounds described herein, and this recruitment is dependent upon the presence of EKLF.

Two compounds were evaluated, compound P and W. Exposure of primary erythroid cells to the high-potency inducer, compound P, resulted in displacement of a repressor complex of HDAC3, NCoR, specifically from the fetal globin gene promoter, with local hyperacetylation of the promoter. Further, exposure to the compound induced recruitment of erythroid kruppel-like factor (EKLF) and Brahma-related gene 1 (Brg1) ATPase proteins to the gamma-globin gene promoter, resulting in selective transcriptional activation of the gamma globin gene. This is a selective effect on the fetal (gamma globin) gene promoter, without generalized widespread epistatic effects or any effects on the beta globin promoter, as other agents tend to cause. The transcription factor EKLF and the remodeling complex Brg1 and Pol II became bound to the promoter in association with gene activation. In contrast, there were no effects on the beta globin gene promoter. These compounds therefore produce highly specific activating effects solely on the globin gene promoter which would be beneficial to induce for therapy of the beta globin gene disorders, and provide a targeted molecular activity.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

Various embodiments of the disclosure could also include permutations of the various elements recited in the claims as if each dependent claim was multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

The invention claimed is:

1. A pharmaceutical composition comprising an effective amount of a compound for treating a blood disorder comprising:

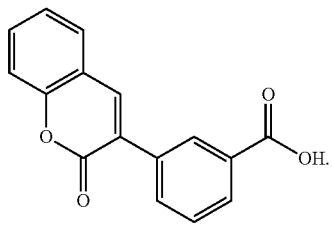 [SMILES: O=C(O)c1cccc(-c2cc3ccccc3oc2=O)c1]

2. The pharmaceutical composition of claim 1, wherein the blood disorder is anemia.

3. The pharmaceutical composition of claim 1, wherein the anemia is sickle cell anemia, beta-thalassemia, neutropenia or thrombocytopenia.

4. The pharmaceutical composition of claim 1, wherein the compound stimulates one or more of fetal hemoglobin production, fetal hematopoiesis, fetal erythropoiesis, fetal myelopoiesis and neutrophil production.

5. The pharmaceutical composition of claim 1, wherein the compound is administered in combination with one or more cytokines.

6. The pharmaceutical composition of claim 5, wherein said one or more cytokine is selected from one or more of the group consisting of EPO, IL-3, GM-CSF, G-CSF, SCF, and IL-6.

7. The pharmaceutical composition of claim 1, further comprising one or more agents selected from the group consisting of pharmaceutically carriers, lubricants, preservatives, wetting agents, diluents, emulsifiers, salts, buffers, coloring agents and flavoring agents.

8. The pharmaceutical composition of claim 1, which is in the form of tablets, capsules, lozenges, troches, hard candies, powders, sprays, creams, salves, suppositories, jellies or syrups.

9. The pharmaceutical composition of claim 1, wherein the compound is present at a therapeutically-effective concentration.

10. The pharmaceutical composition of claim 9, wherein the therapeutically-effective concentration is from about 5% to about 70% by weight or configured for administration at from 0.01 to 100 mg per kg of patient body weight.

11. The pharmaceutical composition of claim 1, which is configured for parenteral or enteral administration to a patient.

12. A pharmaceutical composition comprising an effective amount of a compound for treating a blood disorder comprising:

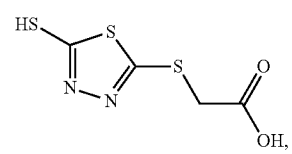 [SMILES: O=C(O)CSc1nnc(S)s1]

in combination with one or more cytokines.

13. The pharmaceutical composition of claim 12, wherein the blood disorder is anemia.

14. The pharmaceutical composition of claim 12, wherein the anemia is anemia, sickle cell anemia, .beta.-thalassemia, neutropenia, and thrombocytopenia.

15. The pharmaceutical composition of claim 12, wherein the compound stimulates fetal hemoglobin production.

16. The pharmaceutical composition of claim 12, wherein the compound stimulates fetal hematopoiesis.

17. The pharmaceutical composition of claim 12, wherein the compound stimulates fetal erythropoiesis.

18. The pharmaceutical composition of claim 12, wherein the compound stimulates fetal myelopoiesis.

19. The pharmaceutical composition of claim 12, wherein the compound stimulates neutrophil production.

20. The pharmaceutical composition of claim 12, wherein said one or more cytokine is selected from one or more of the group consisting of EPO, IL-3, GM-CSF, G-CSF, SCF and IL-6.

21. The pharmaceutical composition of claim 12, further comprising one or more agents selected from the group consisting of pharmaceutically carriers, lubricants, preservatives, wetting agents, diluents, emulsifiers, salts, buffers, coloring agents and flavoring agents.

22. The pharmaceutical composition of claim 12, which is in the form of tablets, capsules, lozenges, troches, hard candies, powders, sprays, creams, salves, suppositories, jellies or syrups.

23. The pharmaceutical composition of claim 12, wherein the compound is present at a therapeutically-effective concentration.

24. The pharmaceutical composition of claim 23, wherein the therapeutically-effective concentration is from about 5% to about 70% by weight or configured for administration at from 0.01 to 100 mg per kg of patient body weight.

25. The pharmaceutical composition of claim 12, which is configured for parenteral or enteral administration to a patient.

* * * * *